US012778569B2

(12) United States Patent
Melilli et al.

(10) Patent No.: US 12,778,569 B2
(45) **Date of Patent: *Nov. 3, 2026**

(54) ARTICULATING STABILIZER ARM WITH DISPOSABLE AND REUSABLE SUBASSEMBLIES

(71) Applicant: Terumo Cardiovascular Systems Corporation, Ann Arbor, MI (US)

(72) Inventors: Bryan Melilli, North East, MD (US); Gregory P. Muennich, Georgetown, MD (US)

(73) Assignee: Terumo Cardiovascular Systems Corporation, Ann Arbor, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 19/192,822

(22) Filed: Apr. 29, 2025

(65) Prior Publication Data

US 2025/0255595 A1 Aug. 14, 2025

Related U.S. Application Data

(63) Continuation of application No. 18/406,806, filed on Jan. 8, 2024, now Pat. No. 12,310,570, which is a continuation of application No. 17/381,315, filed on Jul. 21, 2021, now Pat. No. 11,864,746.

(51) Int. Cl.
*A61B 17/02* (2006.01)
*A61B 17/00* (2006.01)

(52) U.S. Cl.
CPC .. *A61B 17/0206* (2013.01); *A61B 2017/0023* (2013.01); *A61B 2017/0237* (2013.01)

(58) Field of Classification Search
CPC ........ A61B 17/0206; A61B 2017/0023; A61B 2017/0237
See application file for complete search history.

(56) References Cited

U.S. PATENT DOCUMENTS

| | | | |
|---|---|---|---|
| 4,457,300 | A | 7/1984 | Budde |
| 5,772,583 | A | 6/1998 | Wright et al. |
| 6,685,632 | B1 | 2/2004 | Hu et al. |
| 6,860,668 | B2 | 3/2005 | Ibrahim et al. |

(Continued)

FOREIGN PATENT DOCUMENTS

| | | |
|---|---|---|
| DE | 10-2011-114633 | 4/2013 |

*Primary Examiner* — Eduardo C Robert
*Assistant Examiner* — Tara Rose E Carter
(74) *Attorney, Agent, or Firm* — Fish & Richardson P.C.

(57) ABSTRACT

A surgical stabilizer arm includes a reusable base portion and a disposable arm portion. The articulating links that enable the arm to be positioned into arbitrary trajectories are included the disposable portion, thus eliminating the need to clean between the links after a surgical procedure. The disposable portion also includes a tool attachment mechanism and a cable. The reusable portion includes a retractor clamping mechanism, a top plate, a T-shaped base post, a main body, a nosepiece, a threaded drawbar, a thrust bearing assembly, and a threaded handle that can extend or retract the drawbar when rotated. The threaded drawbar may include a slot into which an end of the cable can be inserted, which allows tension to be applied to the cable when the handle is rotated to pull the drawbar into the body of the reusable portion and lock the articulating links in place.

20 Claims, 12 Drawing Sheets

(56) References Cited

U.S. PATENT DOCUMENTS

| | | | | |
|---|---|---|---|---|
| 7,736,307 | B2 | 6/2010 | Hu et al. | |
| 8,092,368 | B2 | 1/2012 | Bertolero et al. | |
| 9,498,198 | B2 | 11/2016 | Hu et al. | |
| 2007/0261320 | A1 | 11/2007 | Lucas | |
| 2009/0216232 | A1 | 8/2009 | Buford, III et al. | |
| 2010/0261971 | A1 * | 10/2010 | Danitz | B25J 9/104 600/204 |
| 2010/0317925 | A1 | 12/2010 | Banchieri | |
| 2012/0010629 | A1 | 1/2012 | Mire et al. | |

* cited by examiner

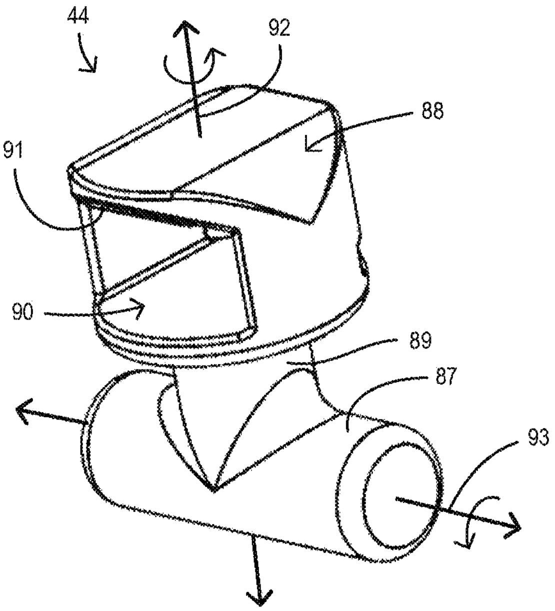
Fig. 24
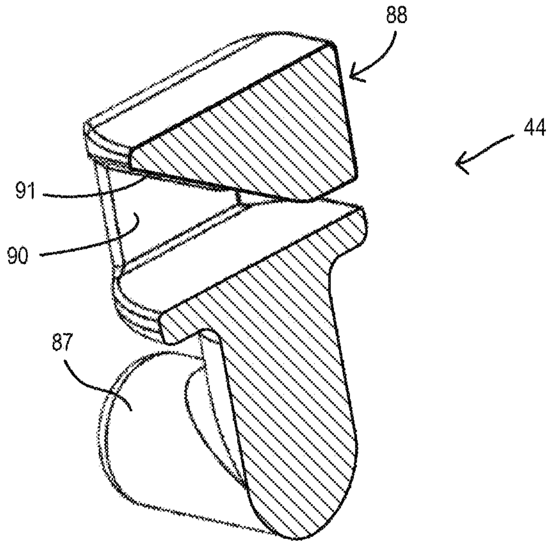
Fig. 25
Fig. 26
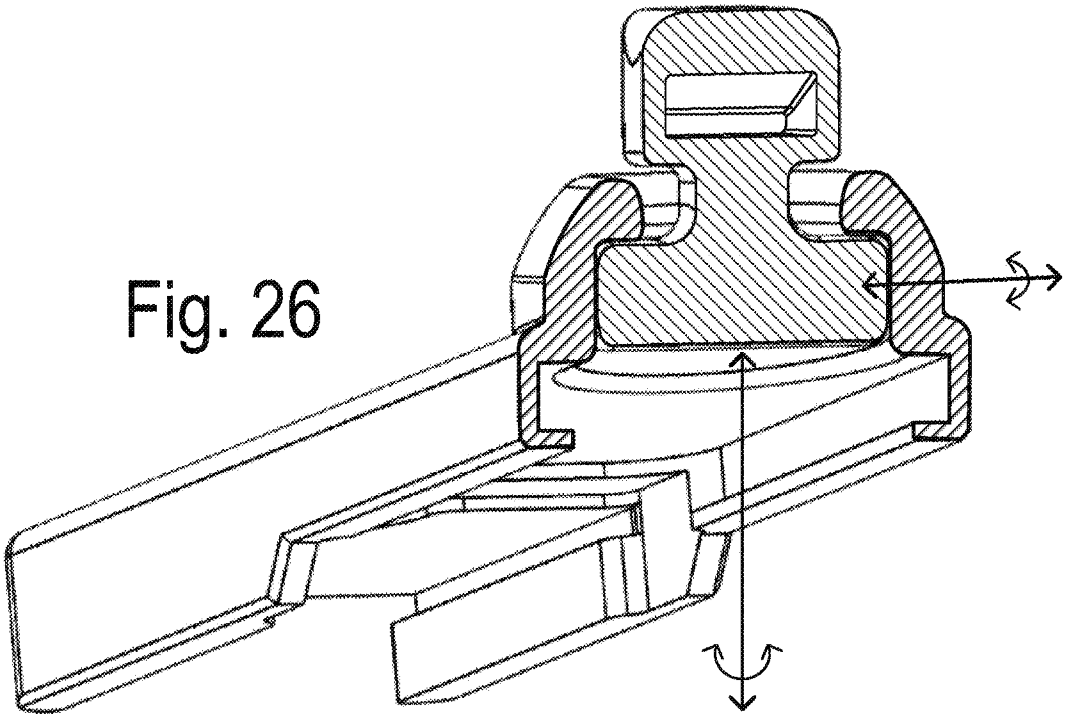

ARTICULATING STABILIZER ARM WITH DISPOSABLE AND REUSABLE SUBASSEMBLIES

CROSS REFERENCE TO RELATED APPLICATIONS

This application is a continuation of U.S. application Ser. No. 18/406,806, filed on Jan. 8, 2024, which is a continuation of U.S. application Ser. No. 17/381,315, filed on Jul. 21, 2021, now U.S. Pat. No. 11,864,746. The contents of the aforementioned applications are hereby incorporated by reference in their entirety.

BACKGROUND

The present disclosure relates in general to an adjustable arm for stabilizing tissues during surgical procedures such as beating heart cardiac surgery, and, more specifically, to a stabilizer arm having reusable and disposable subassemblies.

During cardiac surgery, a sternal retractor is typically mounted over the patient carrying retractor blades to separate overlying tissues to allow access to a surgical site. The frame of the sternal retractor has been used to support surgical components (e.g., mechanical rakes or tissue retractors) at selected positions, as shown in U.S. Pat. No. 5,772,583, for example. An adjustable stabilizer arm that mounts onto a sternal retractor frame (or onto other fixtures or thoracic access devices) may provide an adjustable intermediate support for holding the surgical component at a desired position.

The stabilizer arm may be comprised of various articulating links which are disposed between a quick connector at the distal end (for attaching the surgical component) and a mounting clamp at the proximal end (e.g., for attaching to the fixed sternal retractor). The quick connector provides an end adapter which can grasp a tissue manipulator tool such as a retractor rake. The tool (e.g., rake) may typically be disposable after one use, while the stabilizer arm has typically been reusable after being re-sterilized. An example of a commercially available stabilizer arm is the Hercules™ Stabilizing Arm, sold by Terumo Cardiovascular Systems Corporation of Ann Arbor, Michigan. The articulating links of the stabilizer arm are arranged in a lockable column wherein a central tensioning cable is strung through the links. When the cable is partially tensioned (e.g., by rotating a handle), the links move toward each other to interlock via a series of movable ball and socket joints. The column becomes rigid when the central cable is fully tensioned. Releasing the tension (e.g., by counter-rotating the handle) returns the column to the flexible state. In the relaxed state, enough tension may be maintained to weakly remain in position as the column is adjusted to a desired configuration. The ball and socket joints are generally hemispherical so that side-to-side adjustment angles are available over a wide range.

Significant portions of the hemispherical surfaces are obscured when the links are nested together. In order to re-sterilize at the point of use (e.g., medical facility or hospital), the tension cable must be slackened to spread the links far enough apart from one another in order to clean between links. Thus, the most challenging and time consuming portion of the sterilization process has been the cleaning of the links and the cable between the links. To avoid the associated efforts for sterilization, some stabilizer arms have been marketed as fully disposable. However, a higher cost is incurred when an entire stabilizer arm is discarded and a new unit is consumed for each surgical procedure.

SUMMARY

The present disclosure provides a stabilizer arm with a reusable base portion and a disposable arm portion. The articulating links that enable the arm to be positioned are part of the disposable portion, thus eliminating the need to clean between the links after a surgical procedure. The disposable portion includes a mechanism to interface with either a ball-style or shaft-style tool attachment, a cable, a series of articulating links, and a small retaining sleeve or band that is compressed onto the cable at the end of the links. The reusable portion includes a retractor clamping mechanism, a top plate, a T-shaped base post, a main body, a nosepiece, a threaded drawbar, a thrust bearing assembly, and a threaded handle that can extend or retract the drawbar when rotated. The threaded drawbar may include a slot into which an end of the cable can be inserted, which allows tension to be applied to the cable when the handle is rotated to pull the drawbar into the body of the reusable portion.

More specifically, a primary aspect of the present disclosure provides a stabilizer arm system with first and second subassemblies. The first subassembly (which may be disposable) is comprised of a plurality of articulating links, a tool interface member, and a tension cable. The articulating links each have a central passage, wherein at least some of the adjacent links nest together at slidable mating surfaces adapted for adjustment of the disposable subassembly to a desired trajectory. The tool interface member is disposed at a distal end of the articulating links and is configured to mount a surgical component to be held at a selected position. The tension cable extends through the central passages, wherein a distal end of the tension cable is affixed to the tool interface member, and wherein a proximal end of the tension cable has a radial expansion for retaining the articulating links on the tension cable. The second subassembly (which may be reusable) is comprised of a domed plate, a barrel-shaped main body, a rotator base, a nosepiece, a drawbar, and a handle. The domed plate is configured to be coupled to a fixture, and the domed plate has a hollow dome portion with a top aperture. The barrel-shaped main body has a longitudinal passage, a bottom cavity having a bottom opening and a distal opening, and a cup-shaped flange around the bottom opening configured to nest with an upper surface of the domed portion. The rotator base is disposed in the top aperture and comprises an inverted T-bar captured in the hollow dome, an upper hub rotationally mounted in the bottom cavity, and a deflector surface disposed in the bottom cavity. The nosepiece is slidable in a distal end portion of the longitudinal passage and has a distal surface configured to bear against a proximal end of the articulating links. The nosepiece includes a plunger arm slidably extending into the bottom cavity to slide on the deflector surface of the rotator base. The drawbar is disposed in the longitudinal passage, wherein a distal end of the drawbar has a retainer configured to releasably capture the proximal end of the tension cable. The handle has a distal end disposed in the longitudinal passage and is movably coupled to the drawbar for manually sliding the drawbar in a longitudinal direction to control a tension applied to the tension cable between a partially loaded state and a fully loaded state. When the tension cable is in the partially loaded state then the articulating links are movable at the mating surfaces and the rotator base is movable on the domed plate. When the tension cable is in the fully loaded state then the articulating links are locked at the mating surfaces and the rotator base is locked on the domed plate.

BRIEF DESCRIPTION OF THE DRAWINGS

FIG. 24 is a perspective view of a rotator base.

FIG. 25 is a cross-sectional view of the rotator base.

FIG. 26 is a cross-sectional view of the rotator base disposed in the domed plate.

DETAILED DESCRIPTION OF PREFERRED EMBODIMENTS

Figure 1:
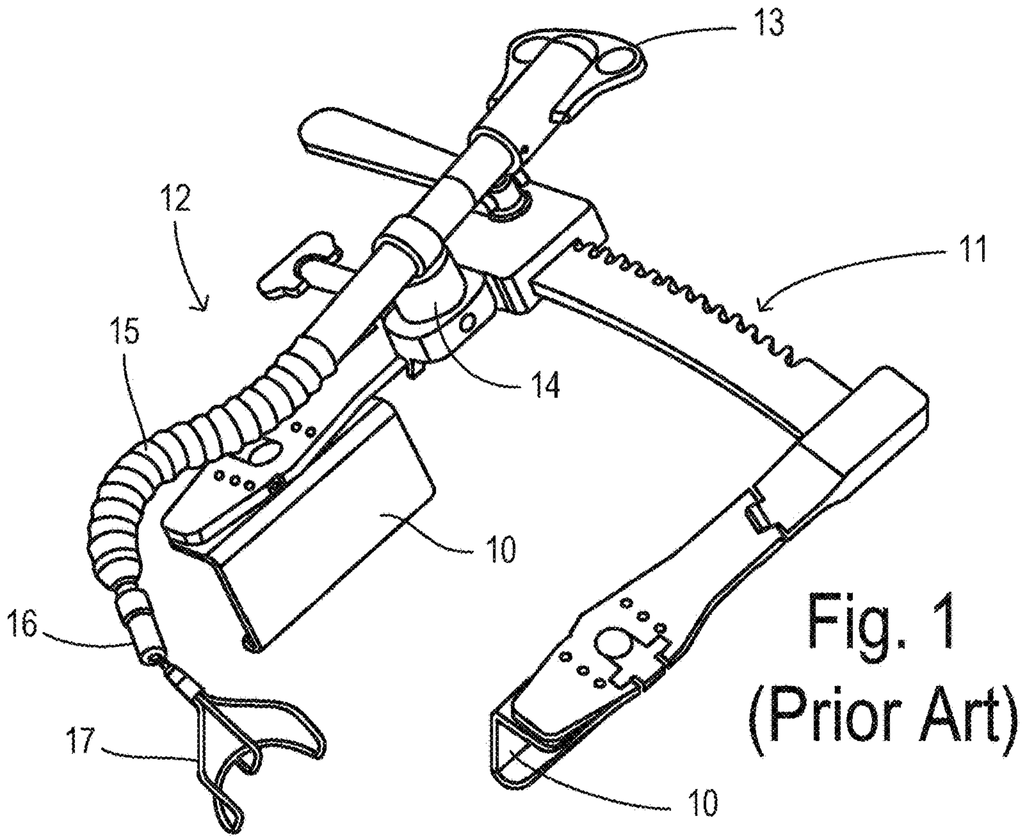
Fig. 1 (Prior Art)
FIG. 1 is a top view of one example of a conventional sternal retractor system.
Figure 2:
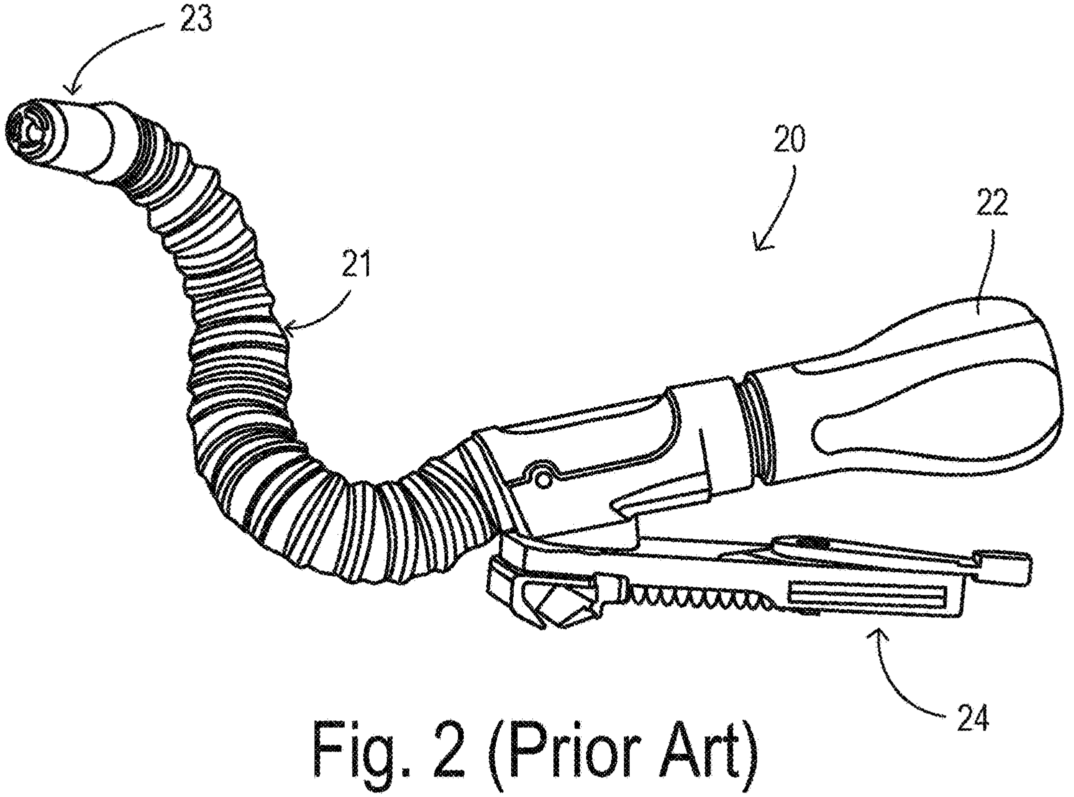
Fig. 2 (Prior Art)
FIG. 2 is a perspective view of a prior art stabilizer arm in a curved configuration.

FIG. 1 shows a prior art sternal retractor with spaced-apart blades 10 carried by an adjustable frame 11. A stabilizer arm 12 has a handle 13, base 14, articulating section 15, and quick-connect mount 16. Base 14 mounts to frame 11, e.g., by a clamp assembly. A retraction tool 17 is adapted for connecting to mount 16 (e.g., by a ball-style or shaft-style capturing mechanism in which tool 17 can be joined or removed without use of any tools). FIG. 2 shows another embodiment of a stabilizer arm 20 with articulating links 21, handle 22, quick-connect mount 23, and a base 24 for clamping to a fixture. A tension cable (not shown) may extend from a proximal end of the stabilizing arm (e.g., from the base or handle) to the distal end (e.g., the quick-connect mount or any other type of fixed final link in the adjustable linkage). A solid metal cable, stranded cable, or a fiber resin can be used. An internal mechanism may adjust tension in the cable in response to rotation of handles 13 or 22. The articulating section may have a plurality of nested, semi-spherical links which can be rotated within one another in order to provide bends in the direction in which the articulating section extends. When the cable is sufficiently slack (i.e., under gentle tension), the links are slidable but when the cable is tightened then the links bind together and the articulating section and an attached tool retain a desired orientation. Most of the component parts of arms 12 or 20 may be comprised of metal, resin, or other materials capable of being re-sterilized and reusable.

Figure 3:
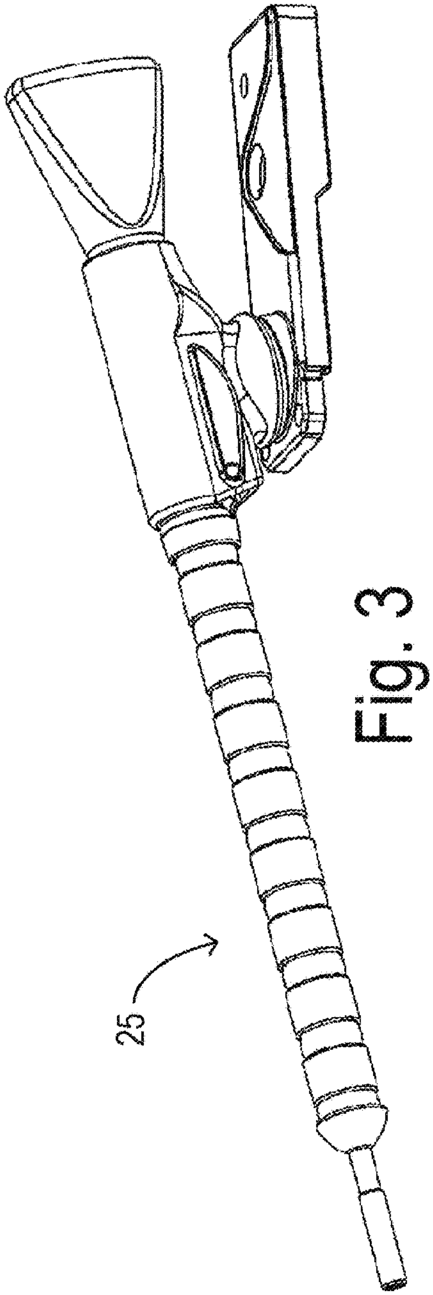
FIG. 3 is a perspective view of one embodiment of a stabilizer arm system of the present disclosure.
Figure 5:
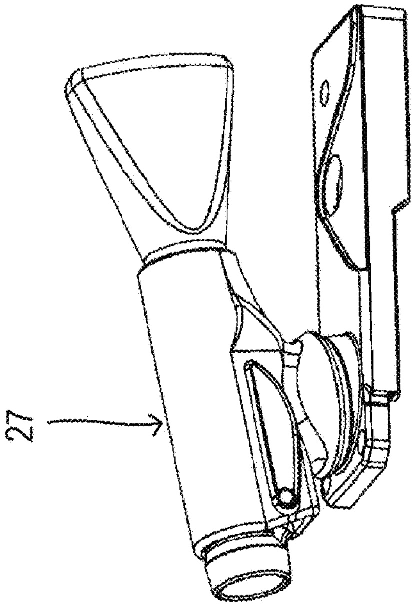
FIG. 5 is a perspective view of a reusable portion of the stabilizer arm system of FIG. 3.
Figure 4:
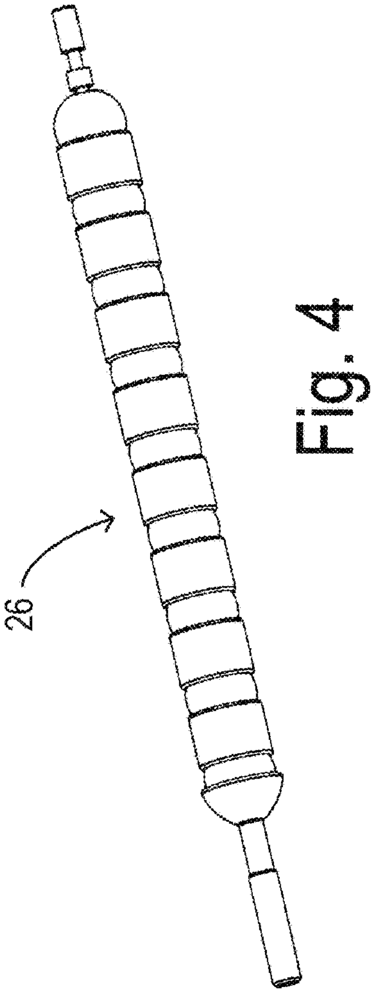
FIG. 4 is a perspective view of a disposable portion of the stabilizer arm system of FIG. 3.

To avoid the challenging re-sterilization of the articulating section without incurring the extra costs of disposing of a complete stabilizer arm, a combination disposable/reusable stabilizer arm 25 shown in FIG. 3 includes a disposable subassembly 26 as shown in FIG. 4 and a reusable subassembly 27 as shown in FIG. 5.

Figure 6:
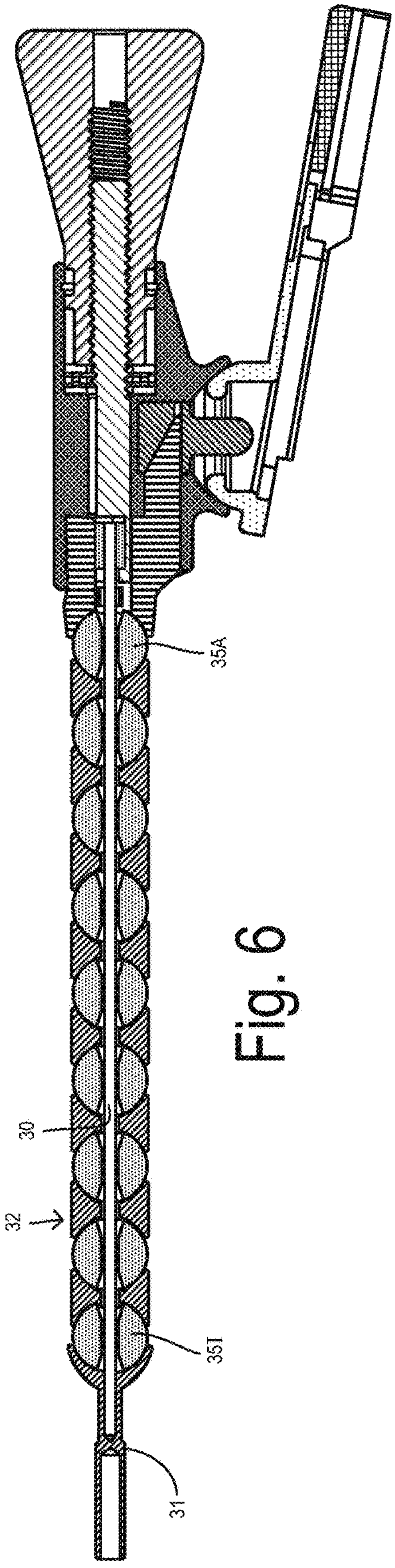
FIG. 6 is a cross-sectional view of the stabilizer arm system of FIG. 3.
Figure 7:
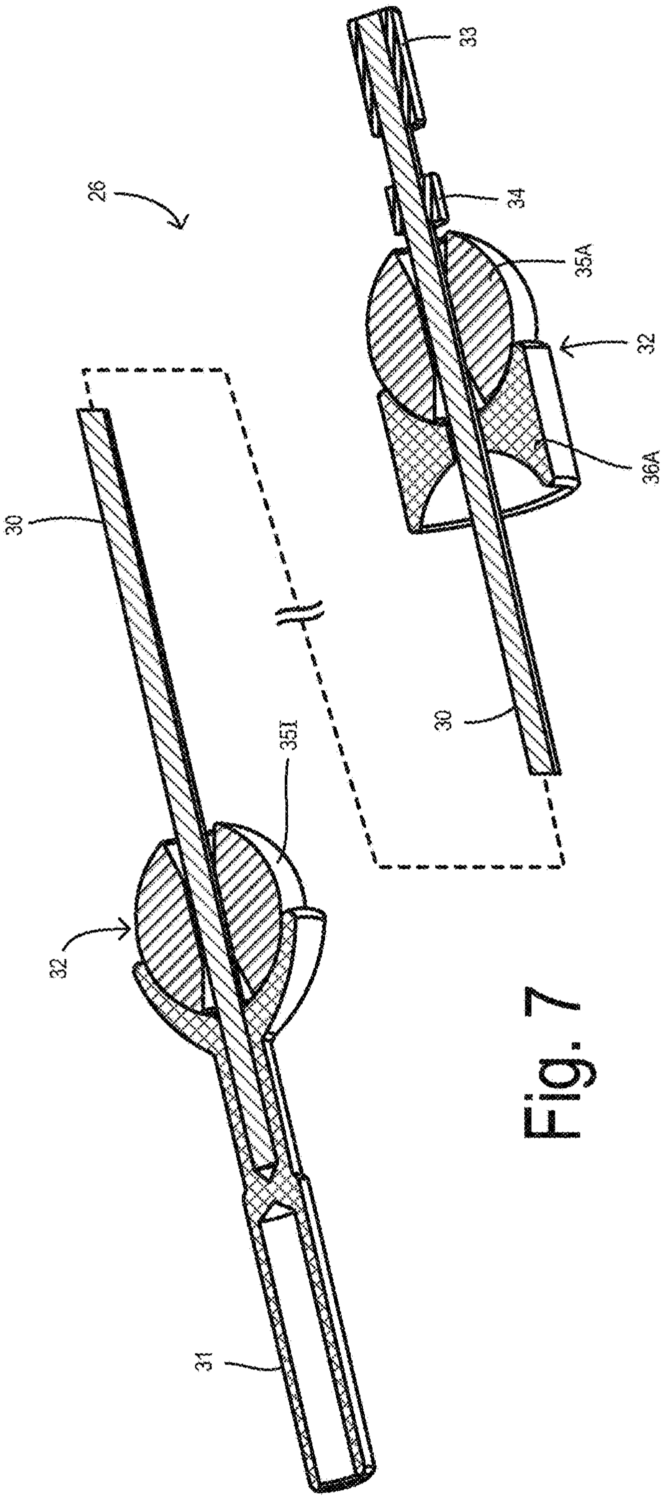
FIG. 7 is a partial cross-sectional view of the disposable portion of FIG. 4.

As shown in FIGS. 6 and 7, disposable portion 26 includes a tension cable 30, a tool interface member 31, a plurality of articulating links 32, a primary swage band 33, and a secondary swage band 34. Articulating links 32 in this embodiment include ball links 35 which are spherically-shaped and cup links 36 which are cylindrically-shaped with hemispherical indents at both ends. A first ball link 35A at a proximal end of links 32 and primary swage band 33 are configured to interface with reusable portion 27 as will be described below. Links 32 of disposable portion 26 could have other types of various shapes, provided that the arm can be articulated at the interfaces between adjacent link in order to enable the arm to be positioned at a variety of angles to best suit the surgical needs. A final ball link 351 at a distal end of links 32 is configured to interface with tool interface member 31. A distal end of tension cable 30 is fixed to tool interface member 31. All of links 32 have a respective central passage or hole through them for cable 30 to pass through. When links 32 are stacked along the cable alternating between the two shapes (e.g., alternating convex and concave spherical sections), the interfaces between each link form an articulating joint. To provide space for articulation, the concave portions of cup links 36 are less than hemispherical in the illustrated embodiment.

Tension cable 30 is an elongated cylindrical body. The proximal end of tension cable 30 that connects to reusable portion 27 has one or more radial expansions which function to retain articulating links 32 on tension cable 30 and/or to enable cable 30 to be grasped by a retainer in reusable portion 27. A single radial expansion can be used to simultaneously provide both functions. For example, primary swage band 33 (i.e., a ferrule or collet) can be fixed onto the proximal end of cable 30 (e.g., by crimping, adhesive, or welding) without using a secondary swage band, whereby swage band 33 attaches to reusable portion 27 and keeps links 32 from falling off cable 30 prior to being attached to reusable portion 27. If present, secondary swage band 34 is disposed closer to links 32 so that the potential spreading apart of links 32 is more limited (keeping links 32 more organized and improving usability since links 32 would be prevented from sliding too close to the connection point). In some embodiments, a selectively releasable connection between cable 30 and reusable portion 27 can be achieved in a manner without a radial extension (e.g., using a chuck or clamp in reusable portion 27). In that case, secondary swage band 34 may be used without primary swage band 33.

Tool interface member 31, which is disposed at the distal end of articulating links 32, is configured to mount a surgical component to be held by stabilizer arm 25 at a selected position. The present disclosure may employ any type of coupling mechanism (such as a quick connect coupling as known in the art using a ball-style and/or a shaft-style attachment) to hold the surgical device. As shown in FIGS. 3-7, tool interface member may be comprised of a proximal bowl-like surface to receive final link 351 on one side, a thinner middle section or cylinder that can be crimped onto the distal end of cable 30, and a cylindrical distal section with an axial bore into which the shaft of a surgical component (e.g., a tissue retractor) can be inserted. The surgical component may be retained by crimping, welding, adhesive, or other means.

Disposable subassembly 26 is adapted for being assembled, sterilized, and packaged as a unit which remains together and is capable of easy handling by the end user. Segregating the articulating links into a subassembly separate from the more complex and costly portions of the stabilizer arm enables an end user to eliminate the cleaning process for the link/cable portion of the device, while maintaining most of the available cost savings by adapting a reusable subassembly to easily couple and uncouple the link/cable portion.

Figure 8:
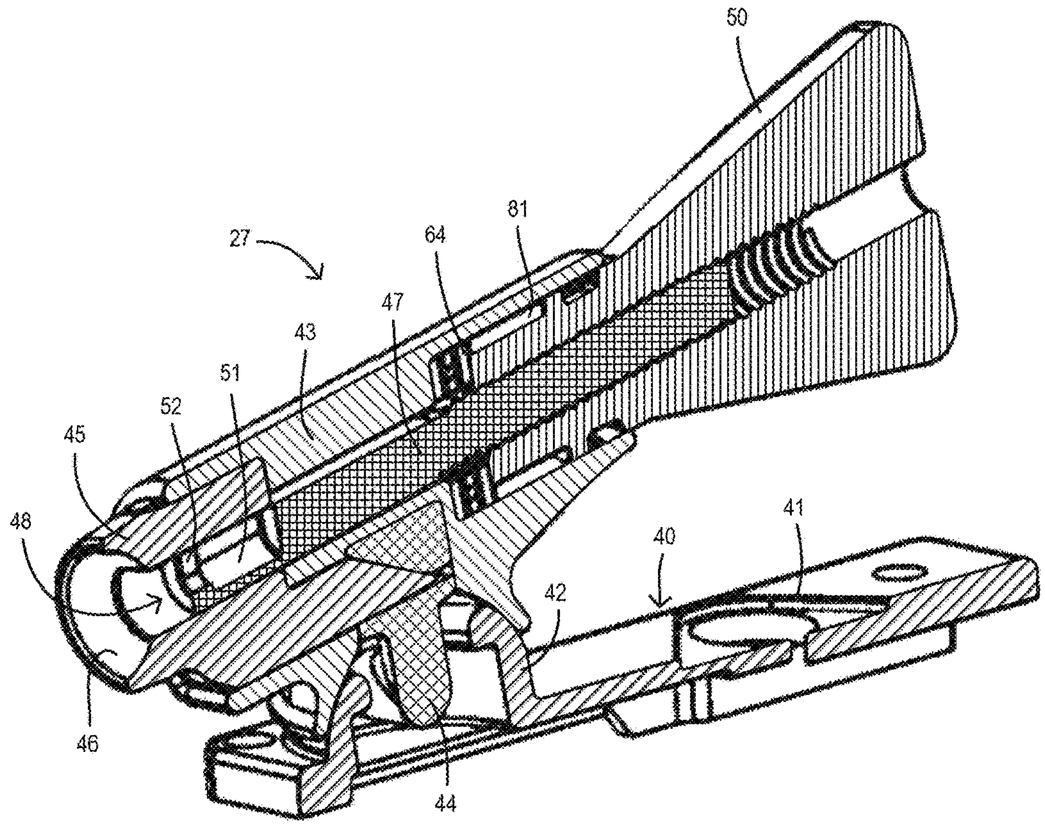
FIG. 8 is a cross-sectional view of the reusable portion of FIG. 5.

As shown in FIGS. 6 and 8, reusable portion 27 includes a domed plate 40 having a clamping end 41 to mount onto a fixture (e.g., a sternal retractor) and having a hollow domed portion 42. A barrel-shaped main body 43 is held on domed portion 42 by a rotator base 44. A slidable nosepiece 45 with a concave (hemispherical) distal surface 46 is configured to bear against a proximal end of articulating links 32 (e.g., by receiving ball link 35A). A drawbar 47 is disposed within main body 43 and nosepiece 45. Drawbar 47 has a retainer 48 configured to releasably capture the proximal end of tension cable 30. A handle 50 has a distal end disposed within main body 43 and is movably coupled to drawbar 47 for manually sliding drawbar 47 in a longitudinal direction to control a tension applied to tension cable 30 between a partially loaded state and a fully loaded state. In the partially loaded state, articulating links 32 are movable at their mating surfaces and rotator base 44 is movable on domed portion 42 of domed plate 40. As explained later, an upper portion of reusable subassembly 27 can move with two degrees of freedom while in the partially loaded state for adjusting the orientation of the proximal portion of articulating links 32. When tension cable 30 is in the fully loaded state then articulating links 32 are locked at their mating surfaces and rotator base 44 is locked at a fixed position on domed portion 42.

Figure 21:
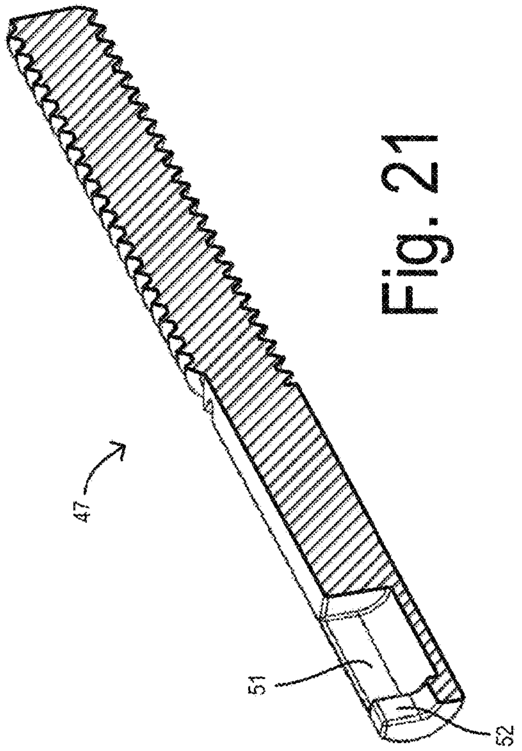
FIG. 21 is a cross-sectional view of the drawbar.
Figure 20:
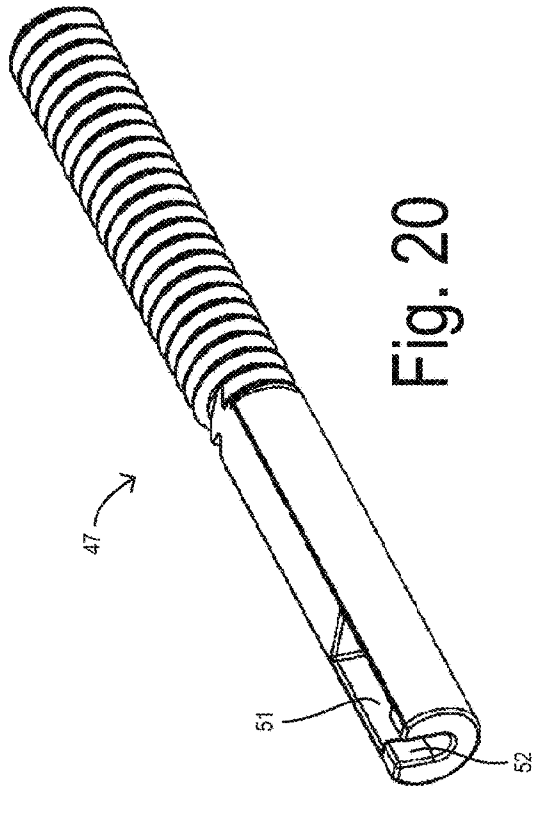
FIG. 20 is a perspective view of a drawbar.

As shown in greater detail in FIGS. 20 and 21, drawbar 47 is partially flattened and has a slot 51 for forming retainer 48 which has a diameter adapted to receive primary swage band 33. A radial notch 52 is provided at the distal end of slot 51 for passing through cable 30. A proximal end of drawbar 47 is threaded for rotation in a threaded passage 53 in handle 50.

Figure 9:
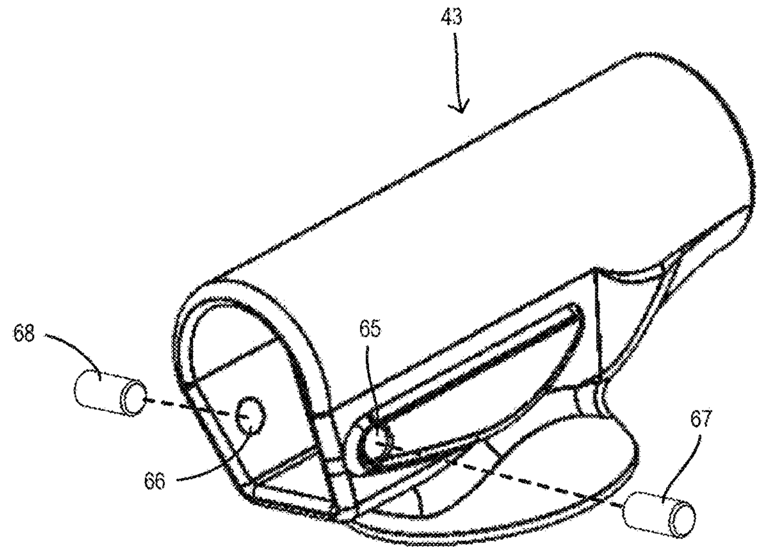
FIG. 9 is a perspective view of a barrel-shaped main body.
Figure 10:
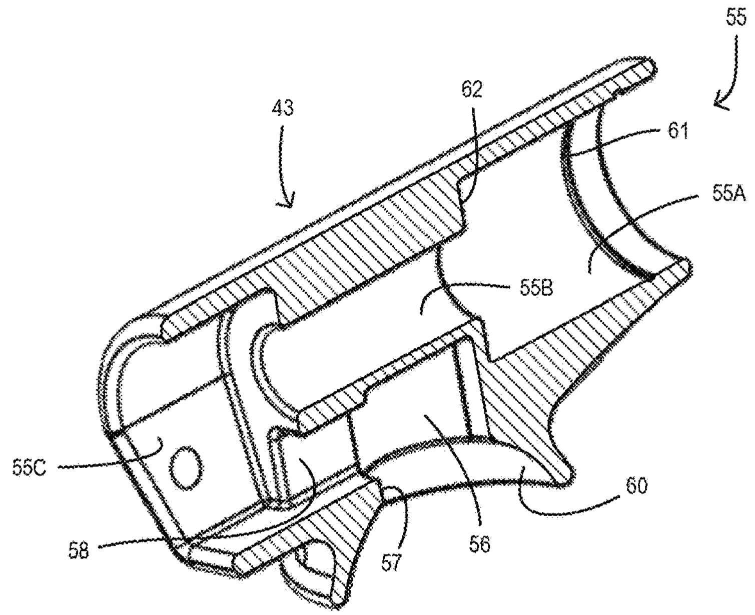
FIG. 10 is a cross-sectional view of the barrel-shaped main body.
Figure 19:
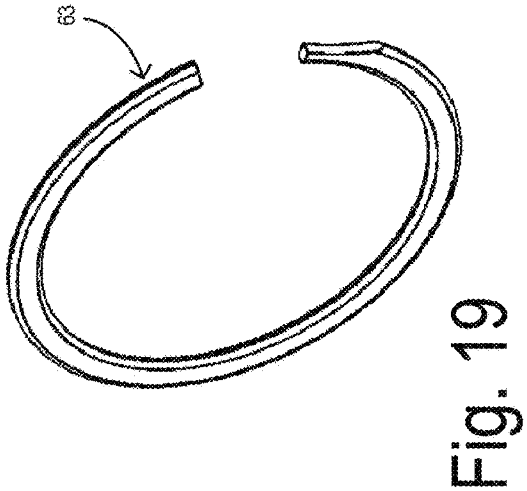
FIG. 19 is a perspective view of a retaining clip for the handle.
Figure 18:
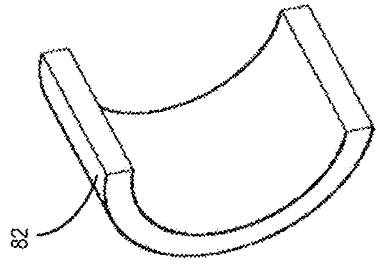
FIG. 18 is a cross-sectional view of the sleeve bearing.
Figure 17:
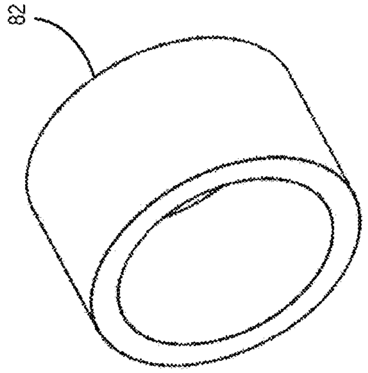
FIG. 17 is a perspective view of a sleeve bearing for providing smooth operation of the handle.

Main body 43 is shown in greater detail in FIGS. 9 and 10. Main body 43 is barrel-shaped around a longitudinal passage 55 with a handle section 55A, a drawbar section 55B, and a nosepiece section 55C. Main body 43 further defines a bottom cavity 56 with a bottom opening 57 and a distal opening 58. A cup-shaped flange 60 around bottom opening 57 has a spherical contour which is configured to nest with an upper surface of domed portion 42. Handle section 55A of passage 55 includes an annular groove 61 for receiving a retaining ring 63 (FIG. 19) and a shoulder 62 for receiving a thrust bearing 64 (FIGS. 15 and 16) for mounting handle 50 for easy rotation. Nosepiece section 55C at the distal end of main body 43 includes holes 65 and 66 for mounting a pair of dowel pins 67 and 68 (e.g., by press fit) to project into section 55C to slidably retain nosepiece 45.

Figure 11:
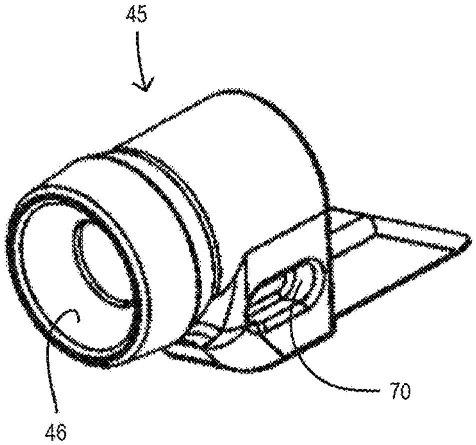
FIG. 11 is a perspective view of a nosepiece.
Figure 12:
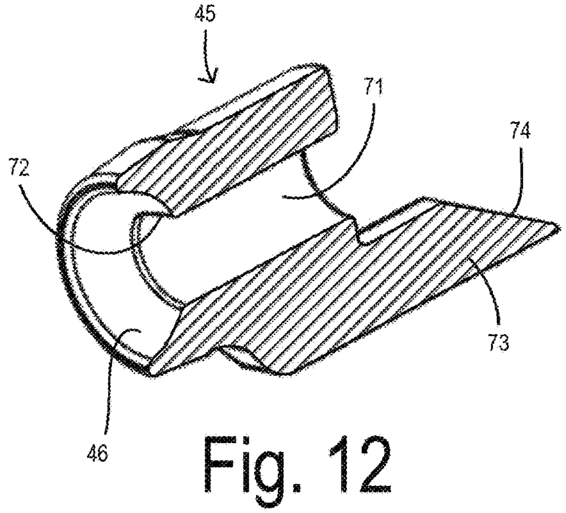
FIG. 12 is a cross-sectional view of the nosepiece.

Nosepiece 45 is shown in greater detail in FIGS. 11 and 12. A guide slot 70 on a side of nosepiece 45 is aligned with hole 65 in main body 43 when pin 67 is fitted in hole 65, which slidably retains nosepiece 45 in nosepiece section 55C (an equivalent slot is present on the opposite side of nosepiece 45 for receiving pin 68). Nosepiece 45 has a central passage 71 which has a generally circular cross section except for a flattened side 72. Passage 71 receives the unthreaded portion of drawbar 47 such that their mutually flattened sides prevent rotation of drawbar 47. More generally, shapes of passage 71 and the section of drawbar 47 received in passage 71 are keyed (e.g. having complementary cross sectional shapes) to limit rotation of drawbar 47 in passage 71. Nosepiece 45 has a plunger arm 73 extending in a proximal direction which is configured to project into bottom cavity 56 by a variable amount as nosepiece slides forward and backward in section 55C. Plunger arm 73 may have a slanted end 74 for deflecting rotator base 44 as described below.

Figure 13:
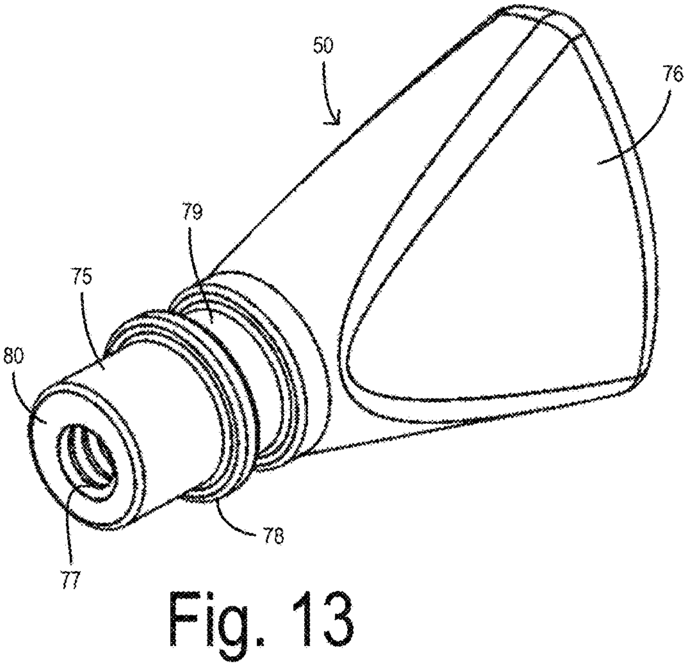
FIG. 13 is a perspective view of a handle.
Figure 14:
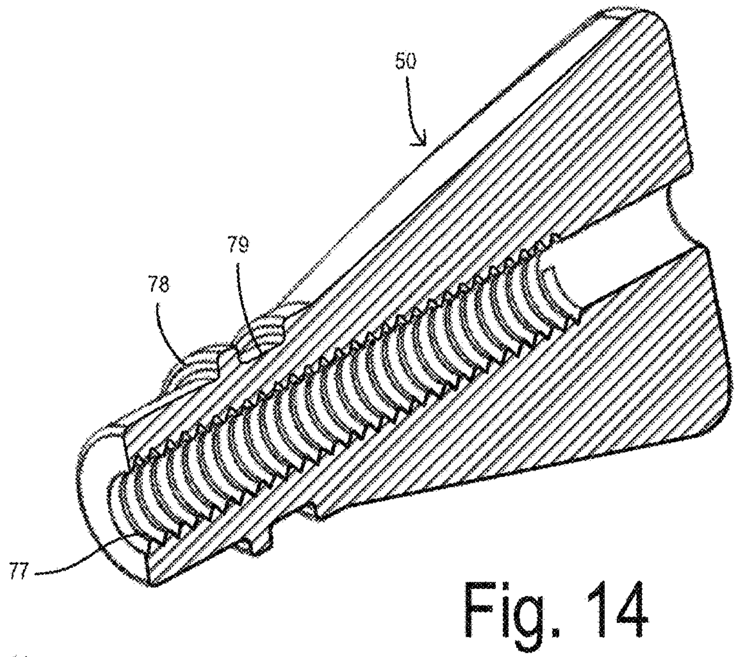
FIG. 14 is a cross-sectional view of the handle.
Figure 15:
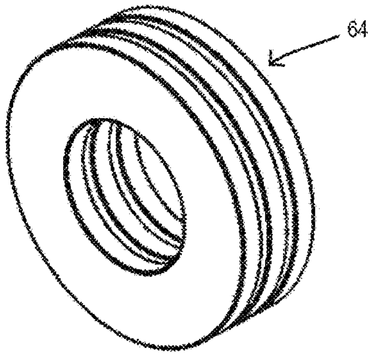
FIG. 15 is a perspective view of a thrust bearing.
Figure 16:
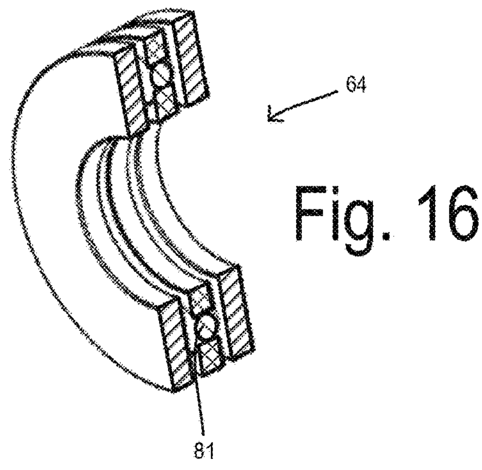
FIG. 16 is a cross-sectional view of the thrust bearing.

Handle 50 is shown in greater detail in FIGS. 13 and 14. A distal-shaft end 75 extends into handle section 55A, and a gripper end 76 is exposed for being manually rotated. A threaded bore 77 receives the threaded end of drawbar 47. A radial flange 78 on shaft end 75 creates an annular groove 79 which receives retaining ring 63 (FIG. 19) to prevent handle 50 from falling off of main body 43. Handle 50 has a distal surface 80 for contacting thrust bearing 64. As shown in FIGS. 15 and 16, thrust bearing 64 may include a race 81 which helps ensure smooth rotation of handle 50. A cylindrical sleeve bearing 82 (e.g., comprised of nylon) is disposed in a gap between flange 78 and thrust bearing 64 to align handle 50 and provide smooth rotation.

Figure 22:
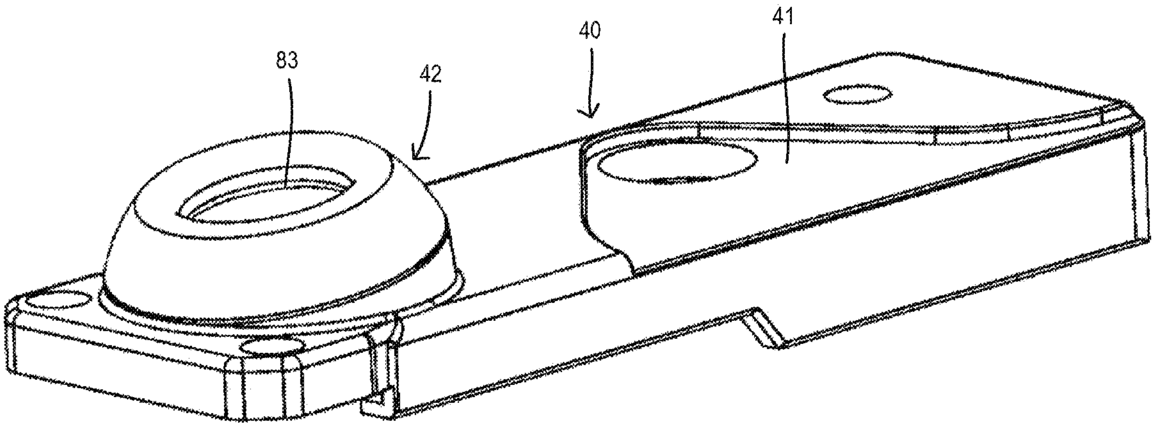
FIG. 22 is a perspective view of a domed plate.
Figure 23:
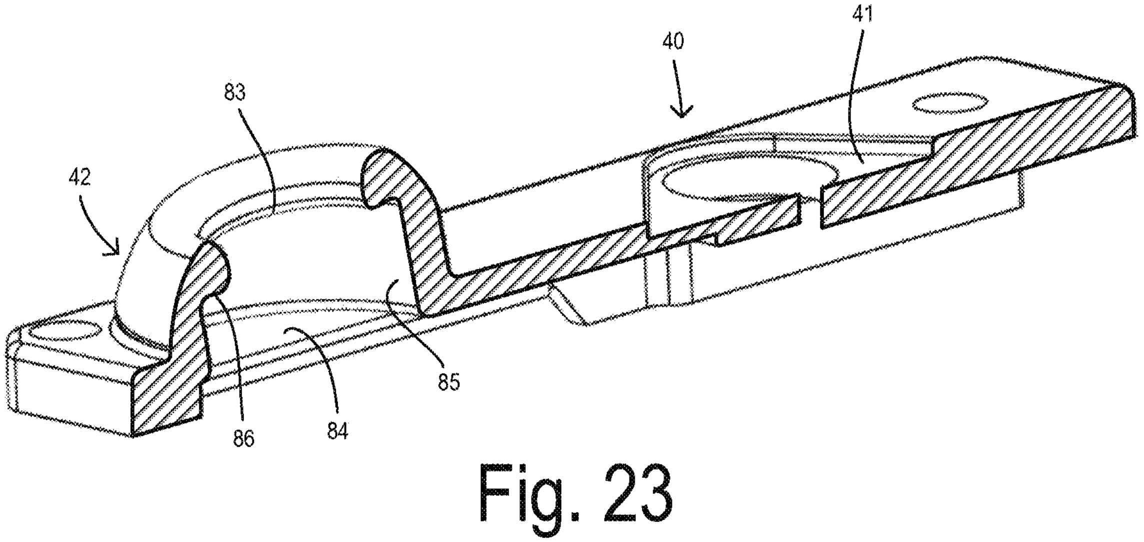
FIG. 23 is a cross-sectional view of the domed plate.

Domed plate 40 is shown in greater detail in FIGS. 22 and 23. Hollow domed portion 42 has a shell-shape with a top aperture 83. An inner recess 84 of hollow domed portion 42 has a cylindrical side wall 85 and a flat upper surface 86.

Rotator base 44 is disposed in top aperture 83 to provide a linkage between domed plate 40 and main body 43 via nosepiece 45. As shown in FIGS. 24 and 25, rotator base comprises an inverted-T bar 87 coupled to an upper hub 88 by a shaft section 89. Hub 88 defines a pocket 90 and a deflector surface 91. Pocket 90 is configured to receive plunger arm 73. During assembly, rotator base 44 is inserted through top aperture 83 so that hub 88 is received through bottom opening 57 into bottom cavity 56 while inverted-T bar 87 is retained in recess 84. Hub 88 and bottom cavity 56 may have keyed profiles (e.g., partially circular with a flattened side) so that hub 88 can only be inserted in a proper orientation. Inverted-T bar 87 has the shape of a cylindrical beam which can rotate within recess 84 around a vertical axis 92 (the axis transverse to flat surface 86) and can rotate (e.g., tilt) forward and backward around a horizontal axis 93 (the axis that is parallel to a longitudinal axis of the cylindrical beam). Domed portion 42 has an upper surface with a convex spherical shape and flange 60 of main body 43 has a concave spherical surface to facilitate the rotation having two degrees of freedom shown in FIG. 26. Since rotator base 44 can tilt forward-to-back but not side-to-side (i.e., since flat upper surface 86 prevents rotation of rotator base 44 around an axis perpendicular to inverted-T bar 87), a third degree of freedom is blocked.

Figure 27:
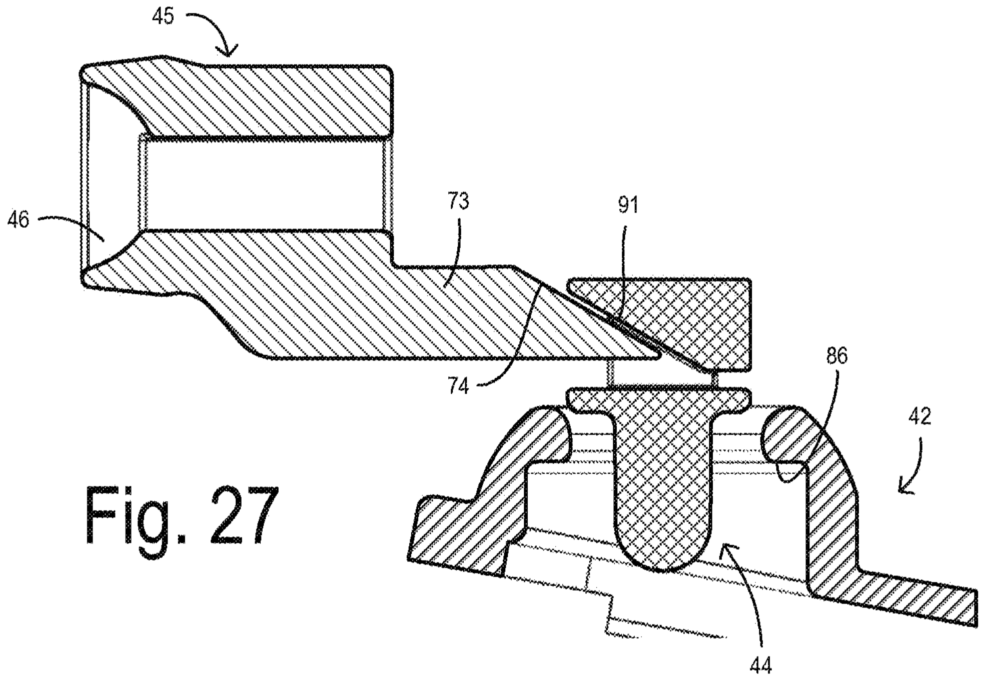
FIGS. 27 and 28 are cross-sectional views of the nosepiece, rotator base, and domed plate depicting movement between unlocked and locked conditions resulting from the tension cable shifting between a partially loaded state and a fully loaded state.
Figure 28:
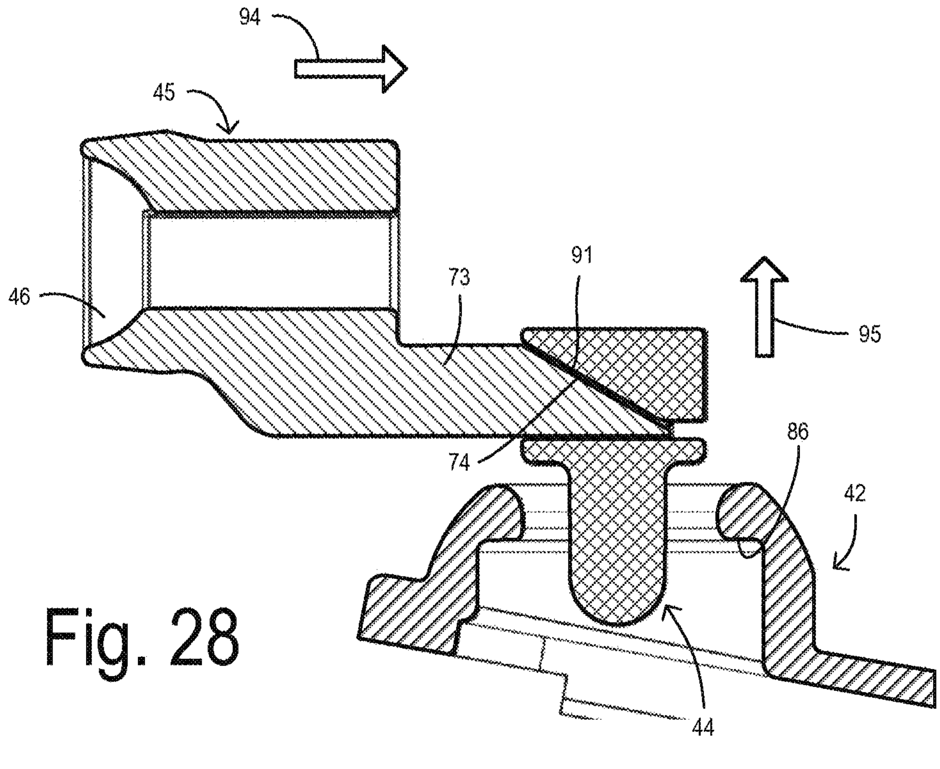

FIGS. 27 and 28 illustrate relative movement among domed plate 40, rotator base 44, and nosepiece 45. FIG. 27 corresponds to a partially-loaded state of the tension cable in which the articulating links are movable at their mating surfaces and rotator base 44 is movable on hollow dome portion 42. FIG. 28 corresponds to a fully-loaded state of the tension cable in which the articulating links are locked at the mating surfaces and rotator base 44 is locked on the hollow dome portion 42. With only gentle tension in the tension cable while in the partially-loaded state, the articulating links are weakly pulled against concave distal surface 46 of nosepiece 45. The slight tension retracts nosepiece 45 in the proximal direction by an amount sufficient to urge rotator base 44 gently upward (via action between slanted end 74 of plunger arm 73 and deflector surface 91) so that light pressure between inverted-T bar 87 and flat upper surface 86 is generated to loosely hold subassemblies 26 and 27 at whatever configuration the user places them in. When drawbar 47 is retracted in response to manual turning of handle 50, the articulating links are drawn against surface 46 so that nosepiece 45 retracts in the direction of arrow 95. As slanted end 74 pushes against deflector surface 91, rotator base 44 rises vertically in the direction of arrow 95 resulting in greater pressure between inverted-T bar 87 and flat upper surface 86 while simultaneously compressing cup-shaped flange 60 against hollow domed portion 42 to lock the components of reusable subassembly 27 into place. Preferably, slanted end 74 has a shape complementary with deflector surface 91 to provide smooth motion. By design, the locking in place of the components in subassembly 27 occurs at the same cable tension that locks the articulated links in place.

Figure 29:
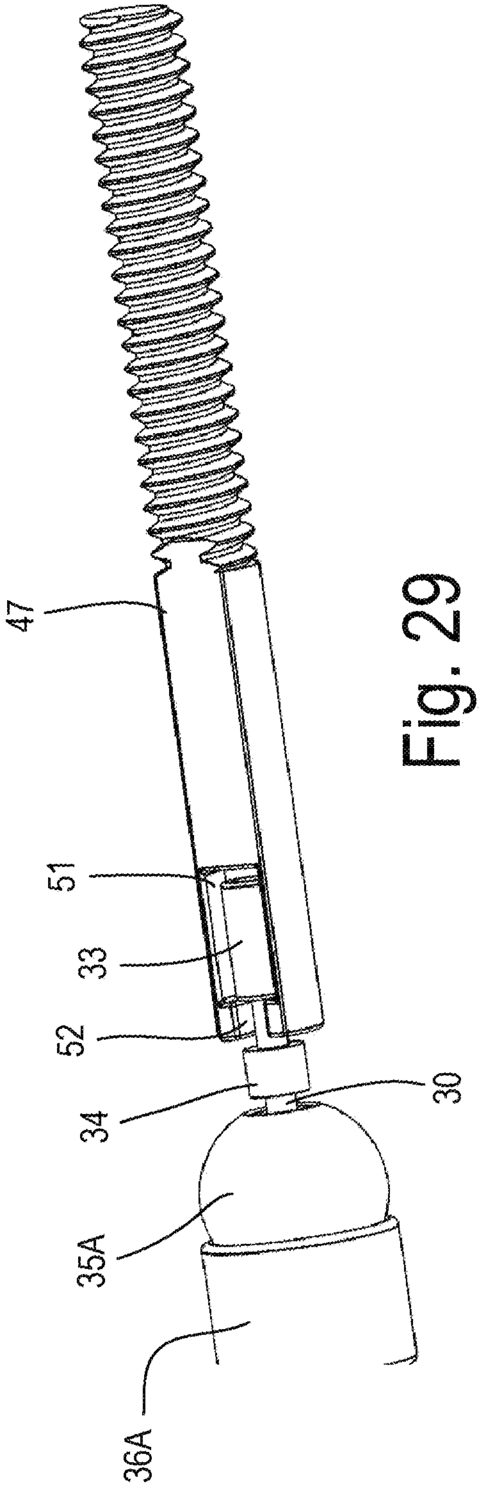
FIG. 29 is a perspective view showing interlocking of the tension cable and swage with the drawbar.
Figure 30:
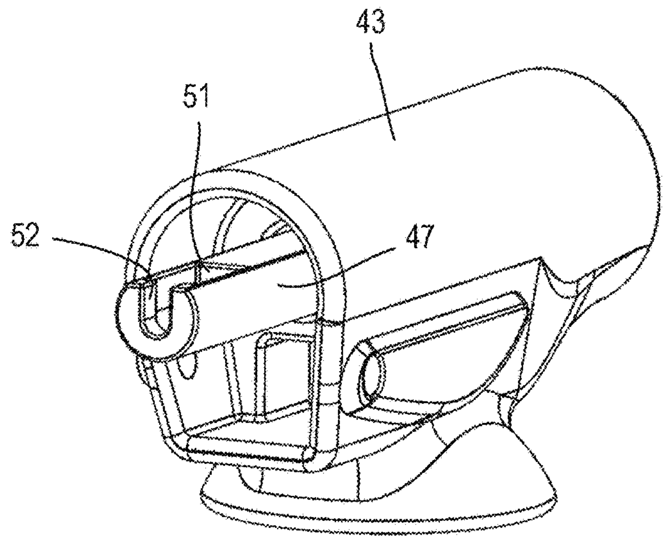
FIG. 30 is a perspective view of the main body with the drawbar installed.
Figure 31:
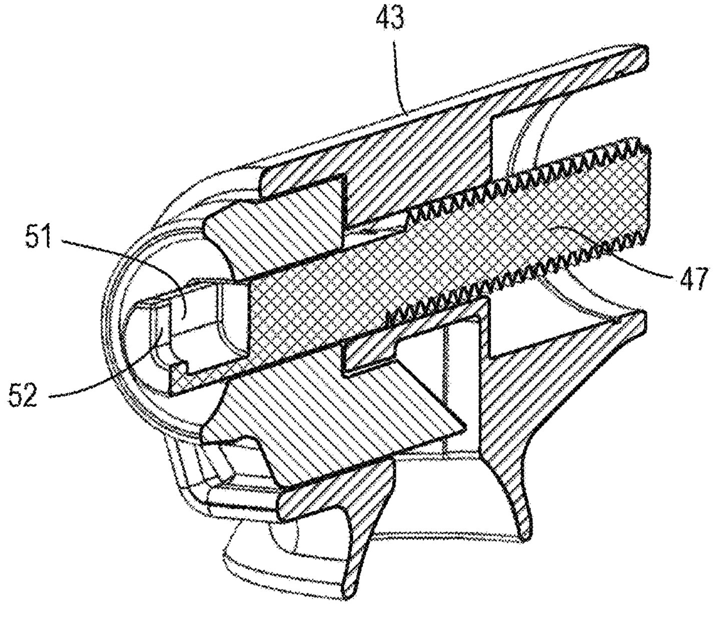
FIG. 31 is a cross-sectional view of the main body, drawbar, and nosepiece is a position for attaching the disposable subassembly.

Interconnection of a disposable subassembly with a reusable subassembly will be explained in connection with FIGS. 29-31. Because of the flattened sides of drawbar 47 and passage 71 of nosepiece 45, slot 51 is open toward the top of the reusable subassembly. The handle is rotated in a direction that causes drawbar 47 to extend in a forward (distal) direction so that slot 51 protrudes beyond the distal end of nosepiece 45 (e.g., FIG. 31). The flattened surfaces prevent rotation of drawbar 47 so that rotation of the handle translates into longitudinal movement of drawbar 47. With slot 51 exposed, swage band 33 on the proximal end of tension cable 30 of the disposable subassembly is inserted into slot 51. Cable 30 passes through notch 52, but swage band 33 is captured in the longitudinal direction because it is larger than notch 52 (the center axis of the tension cable is aligned with a center axis of the drawbar). The handle is rotated in the opposite direction to retract drawbar 47 so that swage band 33 become entrapped in slot 51. With further rotation of the handle, a tension is eventually applied to tension cable 30 once first link 35A of the articulating arm contacts bowl-like surface 46 of nosepiece 45. This movement is what enables the device to lock and unlock the position of the links and the parts of the reusable portion.

Conventional reusable stabilizer arms require the entire device to be cleaned and sterilized between each use. Difficult cleaning between the links is avoided in the present disclosure by modifying a stabilizer arm into two separate subassemblies which can be coupled and uncoupled easily with no tools, wherein a portion having the cable and links is disposable (eliminating the need to carefully clean between the links). Instead, users would be able to simply remove the entire link subassembly from the device and dispose of it. The installation process for the disposable portion is simply inserting a sleeve or swage at the end of the cable into a slot of the drawbar and tightening the handle. Later, it can be removed by loosening the handle and lifting the sleeve out of the drawbar. This cuts down on the amount of work required to reprocess the device before the next procedure. Additionally, this type of modular system is adaptable to multiple styles of arm (e.g., with different lengths, link shapes, etc.) that can all be created to work with the same reusable base portion, thereby enabling better customization for users to select the arm/attachment combinations that best suits their needs.

Conventional stabilizer arms have a base which be adjusted to rotate the main body 360° around a vertical axis, but cannot be tilted forward or backward. The present disclosure adds a second degree of freedom to the connection between the top plate and the main body, improving the ability of the device to be positioned according to the needs of the surgeon.

What is claimed is:

1. A stabilizer arm system for surgical use, the stabilizer arm system comprising:
- a disposable assembly comprising a proximal end and a distal end, the disposable assembly comprising:
  - a plurality of articulating links comprising a proximal link, a distal link, and a plurality of adjacent links between the proximal link and the distal link, each link of the plurality of articulating links comprising a central passage, wherein the adjacent links are slidably coupled at mating surfaces;
  - a tool interface member at the distal end of the disposable assembly, the tool interface member comprising a proximal end coupled to the distal link and a distal end configured to receive a surgical component; and
  - a tension cable extending through the central passages of the plurality of articulating links and comprising a proximal end extending proximally from the proximal link and a distal end coupled to the tool interface member; and
- a reusable assembly configured to releasably couple to the proximal end of the disposable assembly, the reusable assembly comprising:
  - a main body comprising a longitudinal passage;
  - a nosepiece disposed in a distal end portion of the longitudinal passage of the main body, the nosepiece comprising a bore and a distal surface configured to bear against the proximal link of the plurality of articulating links;
  - a drawbar disposed within the longitudinal passage of the main body and extending into the bore of the nosepiece, the drawbar comprising a distal end comprising a retainer configured to releasably couple to the proximal end of the tension cable; and
  - a handle comprising a distal end disposed in the longitudinal passage and movably coupled to the drawbar for moving the drawbar in a longitudinal direction to control a tension applied to the tension cable.

2. The stabilizer arm system of claim 1, wherein the proximal end of the tension cable comprises a first radial expansion configured to retain the plurality of articulating links to the tension cable.

3. The stabilizer arm system of claim 2, wherein the proximal end of the tension cable comprises a second radial expansion spaced from and proximal to the first radial expansion, wherein the second radial expansion is disposed within the retainer of the drawbar when the disposable assembly is coupled to the reusable assembly.

4. The stabilizer arm system of claim 3, wherein the retainer comprises a notch formed in the distal end of the drawbar and a slot extending from the notch and sized to receive the second radial expansion of the tension cable.

5. The stabilizer arm system of claim 1, wherein the handle is configured to rotate to move the drawbar in the longitudinal direction to control the tension applied to the tension cable between a partially loaded state and a fully loaded state.

6. The stabilizer arm system of claim 5, wherein the reusable assembly comprises a plate configured to be coupled to a fixture.

7. The stabilizer arm system of claim 6, wherein the main body comprises a bottom cavity with a bottom opening, the bottom cavity comprises a cup-shaped flange configured to nest with an upper surface of the plate.

8. The stabilizer arm system of claim 7, wherein the reusable assembly comprises a rotator base comprising:

an inverted T-bar captured in a hollow portion of the plate;

an upper hub rotationally mounted in the bottom cavity of the plate; and a deflector surface disposed in the bottom cavity of the plate.

9. The stabilizer arm system of claim 8, wherein the stabilizer arm system is configured such that when the tension cable is in the partially loaded state, the plurality of articulating links are movable at the mating surfaces between the adjacent links and the rotator base is movable on the plate.

10. The stabilizer arm system of claim 8, wherein the stabilizer arm system is configured such that when the tension cable is in the fully loaded state, the plurality of articulating links are locked at the mating surfaces and the rotator base is locked on the plate.

11. The stabilizer arm system of claim 1, wherein the tool interface member comprises a quick connect coupling mechanism for holding the surgical component.

12. A disposable assembly of a stabilizer arm system, the disposable assembly comprising:

a proximal end and a distal end;

a plurality of articulating links comprising a proximal link, a distal link, and a plurality of adjacent links between the proximal link and the distal link, each link of the plurality of articulating links comprising a central passage, wherein the adjacent links are slidably coupled at mating surfaces;

a tool interface member at the distal end of the disposable assembly, the tool interface member comprising a proximal end coupled to the distal link and a distal end comprising a quick connect coupling mechanism for holding a surgical component; and a tension cable extending through the central passages of the plurality of articulating links and comprising a proximal end extending proximally from the proximal link and a distal end coupled to the tool interface member, wherein the proximal end of the tension cable comprises a radial expansion configured to releasably couple to a retainer of a reusable assembly of the stabilizer arm system.

13. The disposable assembly of claim 12, wherein the proximal end of the tension cable comprises a second radial expansion distal to the radial expansion, wherein the second radial expansion is configured to retain the plurality of articulating links to the tension cable.

14. The disposable assembly of claim 12, wherein the tool interface member includes a proximal bowl-shaped surface, a thinner middle section, and a cylindrical distal section with an axial bore for crimping onto the distal end of the tension cable and inserting a shaft of a surgical component.

15. The disposable assembly of claim 14, wherein the quick connect coupling mechanism comprises a ball coupling.

16. The disposable assembly of claim 14, where the quick connect coupling mechanism comprises a shaft coupling.

17. A stabilizer arm system for surgical use, the stabilizer arm system comprising:

a disposable assembly comprising a proximal end and a distal end, the disposable assembly comprising:

a plurality of articulating links comprising a proximal link, a distal link, and a plurality of adjacent links between the proximal link and the distal link, each link of the plurality of articulating links comprising a central passage, wherein the adjacent links are slidably coupled at mating surfaces;

a tool interface member at the distal end of the disposable assembly, the tool interface member comprising a proximal end coupled to the distal link and a distal end configured to receive a surgical component; and a tension cable extending through the central passages of the plurality of articulating links and comprising a proximal end extending proximally from the proximal link and a distal end coupled to the tool interface member; and a reusable assembly configured to releasably couple to the proximal end of the disposable assembly, the reusable assembly comprising:

a main body comprising a longitudinal passage;

a nosepiece disposed in a distal end portion of the longitudinal passage of the main body, the nosepiece comprising a bore and a distal surface configured to bear against the proximal link of the plurality of articulating links;

a drawbar disposed within the longitudinal passage of the main body and extending into the bore of the nosepiece, the drawbar comprising a distal end comprising a retainer configured to releasably couple to the proximal end of the tension cable, the retainer comprising a notch formed in the distal end of the drawbar and a slot extending from the notch and sized to releasably capture the proximal end of the tension cable; and a handle comprising a distal end disposed in the longitudinal passage and movably coupled to the drawbar for moving the drawbar in a longitudinal direction to control a tension applied to the tension cable between a partially loaded state and a fully loaded state.

18. The stabilizer arm system of claim 17, wherein the stabilizer arm system is configured such that when the disposable assembly is coupled to the reusable assembly, the tension cable extends through the notch and a radial expansion of the proximal end of the tension cable is disposed inside the slot, wherein the notch has a diameter smaller than an outer diameter of the radial expansion.

19. The stabilizer arm system of claim 18, wherein the proximal end of the tension cable has a second radial expansion for retaining the plurality of articulating links on the tension cable.

20. The stabilizer arm system of claim 17, wherein the reusable assembly comprises:

a plate comprising an upper surface and a bottom surface configured to be coupled to a fixture;
a rotator base comprising:
an inverted T-bar captured in a hollow portion of the plate; and
an upper hub rotationally mounted in a bottom cavity of the plate,
wherein the main body comprises a bottom cavity with a bottom opening, the bottom cavity configured to nest with the upper surface of the plate,
wherein the stabilizer arm system is configured such that when the tension cable is in the partially loaded state the plurality of articulating links are movable at the mating surfaces between the adjacent links and the rotator base is movable on the plate, and when the tension cable is in the fully loaded state the plurality of articulating links are locked at the mating surfaces and the rotator base is locked on the plate.

* * * * *